United States Patent [19]

Tanaka et al.

[11] 4,448,723
[45] May 15, 1984

[54] ANTIBIOTICS PA-41746-B AND C

[75] Inventors: Kentaro Tanaka; Eiji Kondo; Mikao Mayama; Kouichi Matsumoto; Yoshimi Kawamura, all of Osaka; Naoki Tsuji, Hyogo, all of Japan

[73] Assignee: Shionogi & Co., Ltd., Osaka, Japan

[21] Appl. No.: 432,102

[22] Filed: Sep. 29, 1982

[30] Foreign Application Priority Data

Nov. 10, 1981 [JP] Japan .................. 56-180628

[51] Int. Cl.³ .......................................... C07D 487/04
[52] U.S. Cl. ............................ 260/245.2 T; 424/274; 435/119
[58] Field of Search .................... 260/245.2 T

[56] References Cited

PUBLICATIONS

J. Antibiotics, vol. 35, p. 536 (1982).

Primary Examiner—Mary C. Lee
Attorney, Agent, or Firm—Wenderoth, Lind & Ponack

[57] ABSTRACT

New antibiotics having β-lactamase inhibitory activity, PA-41746-B and C of the formula

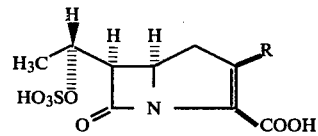

wherein R is carboxymethylsulfinyl (PA-41746-B) or formylsulfinyl (PA-41746-C) and the pharmaceutically acceptable salts being useful as a medicament, a veterinary drug and a disinfectant for inhibiting the growth of gram-positive and gram-negative pathogenic microorganisms and a process for preparing the same, being characterized by cultivating *Streptomyces pluracidomyceticus* in a suitable medium and isolating PA-41746-B and/or PA-41746-C from the culture broth.

3 Claims, 6 Drawing Figures

ANTIBIOTICS PA-41746-B AND C

SUMMARY

New antibiotics having β-lactamase inhibitory activity, PA-41746-B and C of the formula:

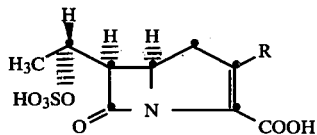

wherein R is carboxymethylsulfinyl (PA-41746-B) or formylsulfinyl (PA-41746-C) and the pharmaceutically acceptable salts being useful as a medicament, a veterinary drug and a disinfectant for inhibiting the growth of gram-positive and gram-negative pathogenic microorganisms and a process for preparing the same, being characterized by cultivating *Streptomyces pluracidomyceticus* in a suitable medium and isolating PA-41746-B and/or PA-41746-C from the culture broth.

The present invention relates to new antibiotics PA-41746-B and PA-41746-C, process for producing the same, and a new species producing the said antibiotics.

The antibiotics in the present invention are new stable antibiotics which have a broad antibacterial spectrum and a β-lactamase inhibiting activity.

The antibiotics PA-41746-B and PA-41746-C has the following structural formula. They are disclosed in J. Antibiotics 35, 536 (1982) as pluracidomycin B and C.

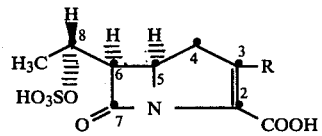

wherein R is SO—$CH_2$COOH (PA-41746-B) or SO—CHO (PA-41746-C).

The present invention includes PA-41746-B and PA-41746-C and their pharmaceutically acceptable salts. There are exemplified the salt with an alkali metal (e.g. sodium, potassium), an alkaline earth metal (e.g. calcium, barium) and the like.

The sodium salts of PA-41746-B and C have the following physical properties.

Figure 1:
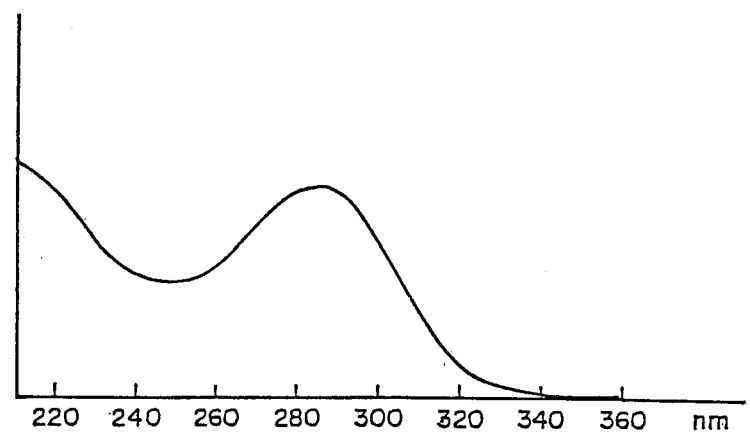
FIG. 1 is an ultraviolet absorption spectrum of PA-41746-B sodium salt.

PA-41746-B sodium salt (a) Ultraviolet absorption spectrum: $\nu_{max}^{H2O}$ 285 nm ($E_{1\,cm}^{1\%}$ 113) (See FIG. 1)

Figure 2:
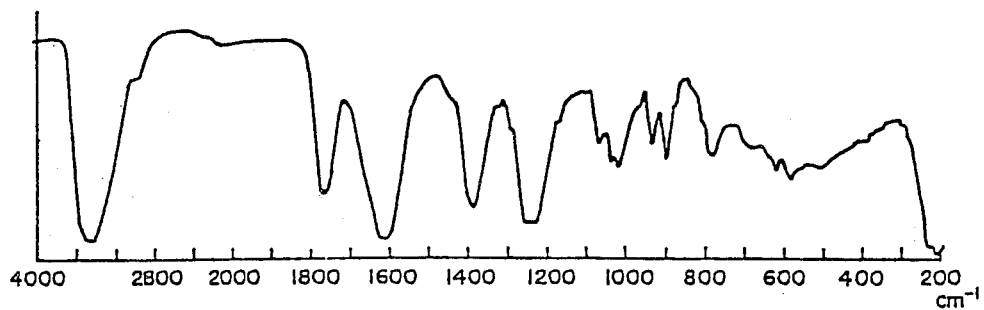
FIG. 2 is an infrared absorption spectrum of PA-41746-B sodium salt.

(b) Infrared absorption spectrum: $\nu_{max}^{KBr}$ 3430, 1755, 1610, 1385, 1250, 1230, 1070, 1040, 1020, 935, 900, 780, 680, 620, 585 cm$^{-1}$ (See FIG. 2)

(c) Circular dichroism spectrum: $\lambda_{nm}([\theta])$ 350(0), 275(+21500), 256(0), 213.5(−55400), 205(−43000)

Figure 3:
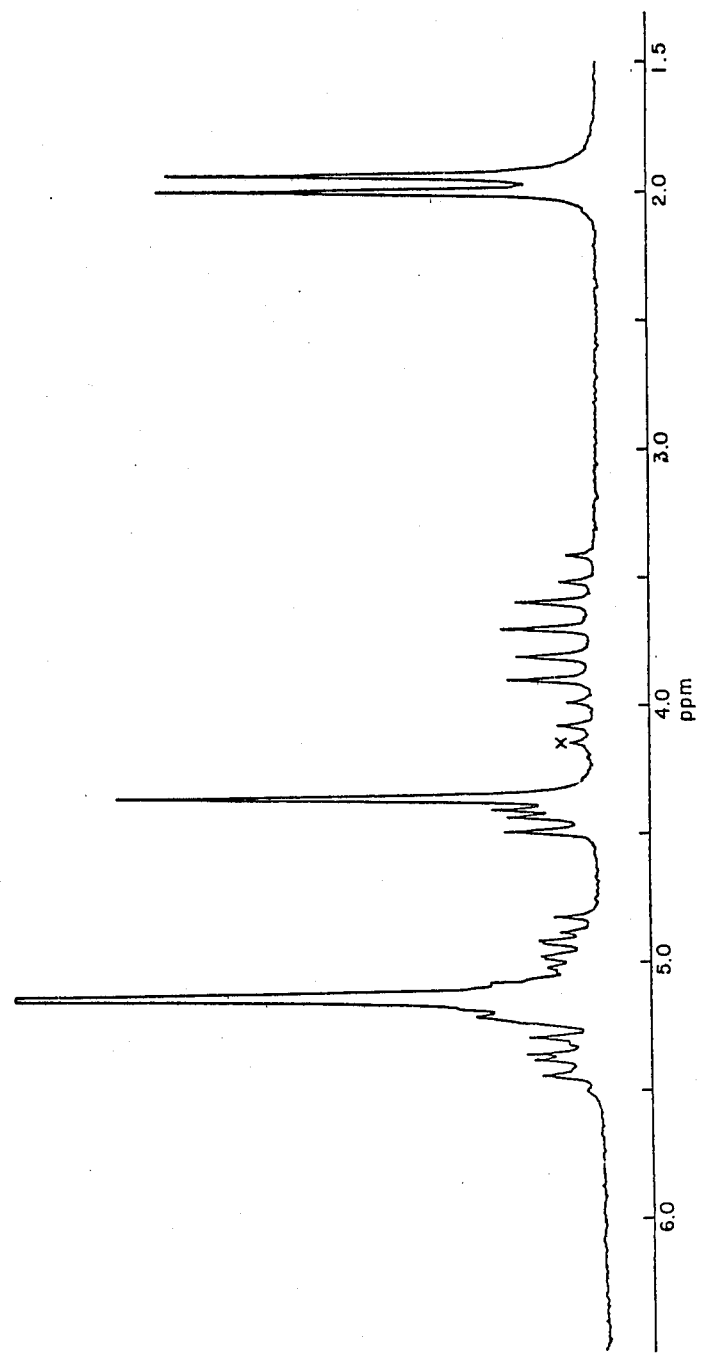
FIG. 3 is an $^1$H-NMR spectrum of PA-41746-B sodium salt.

(d) $^1$H-NMR spectrum: (in $D_2O$, external standard TMS) (J=Hz) 1.97(3H, d, J=6), 3.68(1H, d-d, J=11 and 19), 3.92 (1H, d-d, J=9 and 19), 4.36(2H, s), 4.42(1H, d-d, J=6 and 9), 4.95(1H, m), 5.38(1H, m), ppm (See FIG. 3)

(e) $^{13}$C-NMR spectrum: (in $D_2O$, external standard DSS) 177.5(s), 172.3(s), 166.5(s), 140.6(s), 140.0(s), 74.0(d), 60.2(t), 59.1(d), 54.7(d), 30.5(t), 19.3(q) ppm (DSS=sodium 2,2-dimethyl-2-sylapentan-5-sulfate)

(f) High pressure paper electrophoresis: [Toyo filter paper No. 131 (1×25 cm); 1/30 M phosphate buffer solution (pH 7.0); 12 V/cm; 1.5 hours] Relative mobility 2.7 (Relative mobility of epithienamycin A is set as 1.)

(g) Elementary analysis (%): C, 27.19; H, 3.38; N, 3.49; S, 12.66; Na, 13.55

Figure 4:
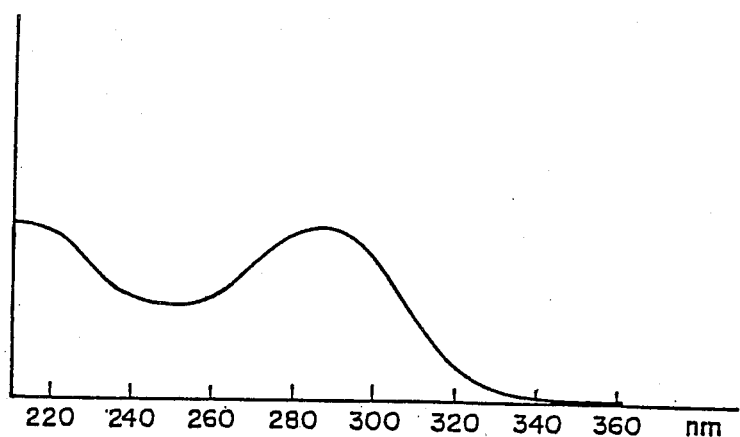
FIG. 4 is an ultraviolet absorption spectrum of PA-41746-C sodium salt.

PA-41746-C sodium salt (a) Ultraviolet absorption spectrum: $\lambda_{max}^{H2O}$ 286 nm ($E_{1\,cm}^{1\%}$ 120) (See FIG. 4)

Figure 5:
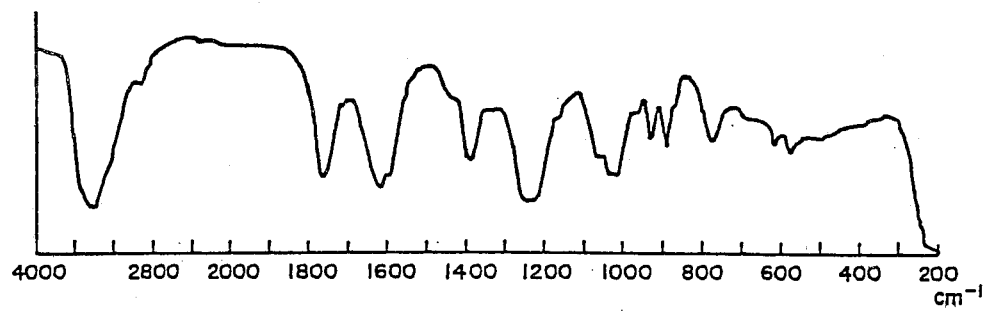
FIG. 5 is an infrared absorption spectrum of PA-41746-C sodium salt.

(b) Infrared absorption spectrum: $\nu_{max}^{KBr}$ 3430, 1770, 1625, 1595, 1395, 1250, 1230, 1070, 1040, 1025, 937, 900, 780, 620, 585 cm$^{-1}$ (See FIG. 5)

(c) Circular dichroism spectrum: $\lambda_{nm}([\theta])$ 350(0), 275(+25000), 253(0), 215(−60200), 205(−38900)

Figure 6:
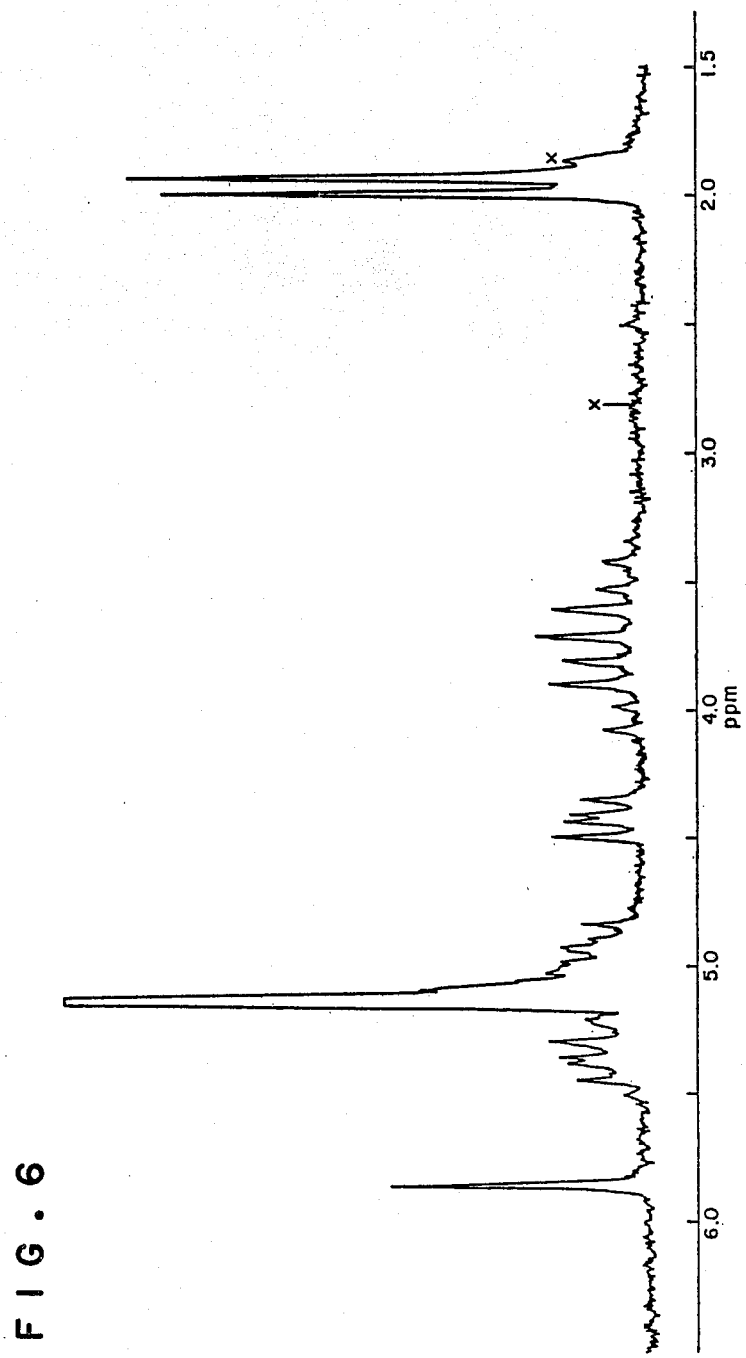
FIG. 6 is an $^1$H-NMR spectrum of PA-41746-C sodium salt.

(d) $^1$H-NMR spectrum: (in $D_2O$, external standard TMS) (J=Hz) 1.97(3H, d, J=6), 3.68(1H, d-d, J=11 and 19), 3.92(1H, d-d, J=9 and 19), 4.42(1H, d-d, J=6 and 9), 4.95(1H, m), 5.38(1H, m), 5.86(1H, s) ppm (See FIG. 6)

(e) $^{13}$C-NMR spectrum: (in $D_2O$, external standard DSS) 177.5(s), 166.4(s), 140.5(s), 140.0(s), 86.5(d), 73.9(d), 59.2(d), 54.7(d), 30.4(t), 19.3(q) ppm (f) High pressure paper electrophoresis [Toyo filter paper No. 131 (1×25 cm); 1/30 M phosphate buffer solution (pH 7.0); 12 V/cm; 1.5 hours] Relative mobility 1.9 (Relative mobility of epithienamycin A is set as 1)

Many carbapenem antibiotics have been known. The compounds having a substituent —CH($OSO_3H$)—$CH_3$ at $C_6$ position in the above formula being known in references are the following three compounds; MM 4550

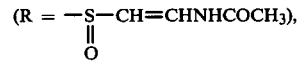

MM 13902 (R=—S—CH=CHNHCOCH$_3$) and MM 17880 (R=—S—$CH_2CH_2$—NHCOCH$_3$).

The antibiotic of this invention has the same nucleus as the above compounds do but are different in the substituent (R) at $C_3$ position. Namely, PA-41746-B has a $CH_2$ in the R and PA-41746-C has a CH in it but neither contains NHCOCH$_3$. In this point, the compounds of this invention are different from the known carbapenem antibiotics having R of cysteamine derivatives. The chemical structures of PA-41746-B and PA-41746-C are as follows:

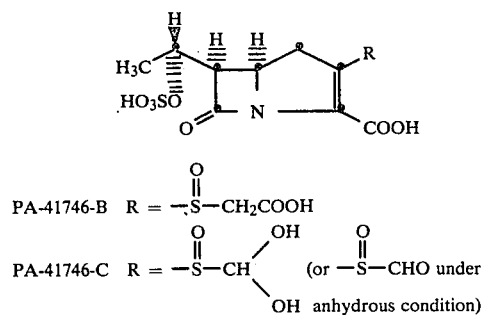

PA-41746-B  R = —S—CH₂COOH $$PA\text{-}41746\text{-}C \quad R = -\overset{O}{\underset{\|}{S}}-\overset{OH}{\underset{OH}{CH}} \quad (\text{or } -\overset{O}{\underset{\|}{S}}-CHO \text{ under anhydrous condition})$$

A fermentation process for preparing PA-41746-B and PA-41746-C is shown below. The production of PA-41746-B and PA-41746-C consists of cultivating a PA-41746-B and/or PA-41746-C-producing strain in a nutrient medium under aerobic condition and isolating the PA-41746-B and/or C from the fermentation broth.

The composition of the culture medium and the conditions for the fermentation follow the generally known ones for producing antibiotics. The medium essentially consists of carbon sources, nitrogen sources and inorganic salts. Vitamines, precursors and other materials may be optionally added to stimulate the production of PA-41746-B and PA-41746-C. Examples of carbon sources are glucose, starch, dextrin, glycerol, molasses, organic acids and the like, which are used singly or in combination. Examples of nitrogen sources are soybean meal, corn steep liquor, meat extract, yeast extract, cotton seed flour, peptone, wheat germ, ammonium sulfate, ammonium nitrate; they are used singly or in combination. Inorganic salts may be selected from calcium carbonate, sodium chloride, potassium chloride, magnesium sulfate, cobalt chloride, various phosphate salts and the like. They are added to the medium if the occassion demands.

Fermentation may be carried out in the same conditions as these used for the production of usual antibiotics; for example, a liquid medium, a submerged aerobic condition, especially for mass production, and the like. The pH of the medium is preferred to be about 5.5 to 8.5. The temperature may be kept at about 20°–40° C., preferrably about 20°–32° C.

Fermentation period depends on the production scale. It takes about 20 to 80 hours in a large scale production.

The antibiotics PA-41746-B and C can be isolated from the fermentation broth by the usual methods for isolating and collecting usual fermentation products. Any conventional method such as filtration, centrifugation, adsorption and desorption with ion exchange resins, chromatography with various active adsorbents, extract with suitable organic solvents of every kind. The procedures may be combined in an appropriate order. Suitable stabilizing agent may be added during the isolating procedure to avoid the decomposition of PA-41746-B and/or C.

The strain PA-41746 of this invention is an actinomycete isolated from a soil sample. The microbiological properties are as follows:

(a) Morphological properties (cultured on Bennett's agar medium at 28° C. for 14 days)

The microorganism grows well on Bennett's agar medium and forms comparatively abundant aerial hyphae on which spores are borne. Spore-bearing hyphae are formed on aerial hyphae and branch simply from main stem to side branches of which ends are short spiral and adjacent to spore chains. The spore chains are short. The number of spores per chain are almost 20 and less. The surface of the spores is mostly smooth under electron microscopy but some are observed to be rough. The spores are oval. Any of sporangium, flagellated spore or sclerotium is not observed. No split by fragmentation is observed in substrate hyphae.

(b) Properties on various media (cultivated at 28° C. for 14 days)

TABLE 1

| Medium | Growth | Aerial Hyphae Growth | Aerial Hyphae Color | Color of substrate Hyphae | Soluble Pigment |
|---|---|---|---|---|---|
| Sucrose Nitrate Agar Medium | Well | None | — | Pale Yellowish brown | None |
| Glucose Asparagine Agar Medium | " | Well | Pale brown | Pale Yellowish brown | " |
| Glycerol Asparagine Agar Medium | Fair | Slightly formed | White | Pale Yellowish brown | " |
| Inorganic salt Starch Agar Medium | Well | None | — | Pale Yellowish brown | " |
| Tyrosine Agar Medium | " | None | — | Pale Yellowish brown | Light brown to grayish brown |
| Nutrient Agar Medium | Slight | None | — | Pale Yellowish brown | None |
| Yeast extract Malt extract Agar Medium | Well | Well | Pale brown | Yellowish brown | Yellowish brown (Slight) |
| Oatmeal Agar Medium | Fair | Fair | Pale brown | Pale Yellowish brown | None |
| Bennett's Agar Medium | Well | " | Pale brown | Yellowish brown | " |

The expression of the color depends on "Guide to color standards" published by Japan Color Institute.

(c) Physiological properties
Liquefaction of gelatin: Positive
Hydrolysis of starch: Positive
Tyrosinase reaction: Negative
Production of melanoid pigment: Negative
Coagulation of milk: Negative
Peptonization of milk: Positive (d) Utilization of carbohydrates
Carbohydrates resulting good growth: D-xylose, D-glucose, D-fructose, sucrose, L-rhamnose.
Carbohydrate resulting fair growth: L-arabinose
Carbohydrates resulting slight growth: Innositol, raffinose.

(e) Growth temperature (cultured on Bennett's agar for 14 days)
10° C.: slight growth without aerial hypha
28° C.: good growth and good formation of aerial hyphae
37° C.: good growth without aerial hypha
45° C.: no growth It is obvious from the above properties that strain PA-41746 belongs to Genus Streptomyces.

The comparison of strain PA-41746 with the similar strains are shown below.

The references for the similar strains are as follows:

The actinomycetes, vol. 2 (1961), International Journal of Systematic Bacteriology vol. 18 (1968), vol. 19 (1969), vol. 22 (1972), Bergey's Manual of Determinative Bacteriology 8th edition (1974) and other references describing new species of actinomycetes. As the result, Streptomyces daghestanicus [Bergey's Manual of Determinative Bacteriology 8th Ed, page 814 and International Journal of Systematic Bacteriology vol. 18, page 104] is found to be mostly similar to strain PA-41746. The comparative test of strain PA-41746 and Streptomyces daghestanicus reveals the following differences.

TABLE 2

| Item for comparison | Strain PA-41746 | St. daghestanicus |
|---|---|---|
| Formation of Aerial Hyphae | | |
| Glucose Asparagine Agar Medium | Well | None |
| Tyrosine Agar Medium | None | Well |
| Spore Form Physiological Properties | Oral | Short cylindrical |
| Liquefaction of Gelatin | Positive | Negative |
| Utilization of Sugar | | |
| Sucrose | Positive | Negative |
| Growth Temperature (45° C.) | None | Good growth without aerial hyphae |

The above comparison brings the conclusion that strain PA-41746 and the similar strain Streptomyces deghestanicus belong to different species each other.

It is determined that strain PA-41746 is a new species belonging to Genus Streptomyces. Then, the strain PA-41746 was named Streptomyces pluracidomyceticus sp. nov.

The strain PA-41746 has been deposited with Fermentation Research Institute at Yatabe-machi, Tsukuba-gun, Ibaragi Pref. since April 17, 1981. The accession number was FERM P-5964 at first and changed to FERM BP-174 at Sept. 6, 1982 since the deposit was transfered to the deposit under Budapest Treaty.

This invention includes the utilization of the above strain PA-41746 as well as the use of any microbes belonging to Streptomyces and producing antibiotic PA-41746-B and/or C.

The antibiotics of this invention, PA-41746-B and PA-41746-C have wide range of anti-microbial spectrum and are effective against both gram-positive and gram-negative bacteria with strong $\beta$-lactamase inhibitory activity. Therefore, they are useful as a medicament, a veterinary drug and a sterilizer. The following show the anti-mictobial spectra and $\beta$-lactamase inhibitory activities of PA-41746-B and C.

(A) ANTI-MICROBIAL SPECTRUM

TABLE 3

| Test Microorganism | Minimum Inhibitory Concentration ($\mu$g/ml) | |
|---|---|---|
| | PA-41746-B | PA-41746-C |
| Staphylococcus aureus 209P JC-1 | 50 | 25 |
| Streptococcus pneumoniae I | 12.5 | 12.5 |
| Escherichia coli NIHJ JC-2 | 6.25 | 12.5 |
| Klebsiella pneumoniae | 12.5 | 25 |

TABLE 3-continued

| Test Microorganism | Minimum Inhibitory Concentration ($\mu$g/ml) | |
|---|---|---|
| | PA-41746-B | PA-41746-C |
| SRL-1 Klebsiella sp. 363(R) | 6.25 | 6.25 |
| Proteus mirabilis PR-4 | 25 | 12.5 |
| Enterobacter cloacae 233 | 100 | >100 |
| Pseudomonas aeruginosa ATCC 25619 | >100 | >100 |

Note:
Inoculum size $10^6$ cells/ml (B) $\beta$-LACTAMASE INHIBITORY ACTIVITY

TABLE 4

| Source of $\beta$-Lactamase | Minimum Effective Concentration($\mu$g/ml) | |
|---|---|---|
| | PA-41746-B | PA-41746-C |
| Enterobacter cloacae 92*[1] | 0.008 | 0.008 |
| Klebsiella sp. 363*[2] | 0.008 | 0.004 |

*[1]producing $\beta$lactamase of cephalosporinase type
*[2]producing $\beta$lactamase of penicillinase type Accordingly, PA-41746-B and C may be orally or parenterally administered to human or animals. They may be formed to tablets, capsules, powder and the like in admixture with diluents, stabilizing agents, preservatives, wetting agents, detergents and the like for oral administration. They can also be parenterally administered in the form of, for example, injection, ointment and suppository. The dosage of these antibiotics is generally about 1/10 time to several times of cefalotin though it depends on the purpose of treatment. For example, the daily dosage to a human adulst is about 0.1 to about 10 g in subcutaneous injection. PA-41764-B and C can synergistically increase the anti-microbial activity of $\beta$-lactam antibiotics against $\beta$-lactamase-producing bacteria because of the $\beta$-lactamase inhibitory activity. Therefore, PA-41746-B and C may be used with known $\beta$-lactam antibiotics such as penicillins (e.g. benzylpenicillin, phenoxymethylpenicillin, carbenicillin, ampicillin, amoxycillin and the like) and cephalosporins (e.g., cefaloridine, cefalotin, cefazorin, cefalexin, cefoxitin, cefacetrile, cefamandole, cefapirin, cefradine, cefaloglycin, ceftezol, cefatrizine, cefmetazol and the like).

The following example is given solely for the purpose of illustration and are not to be construed as limitation of the present invention.

EXAMPLE (a) Fermentation process

A seed culture of Streptomyces pluracidomyceticus (FERM BP-174) was inoculated in a 2-liter Erlenmeyer flask containing 800 ml of a medium (0.5% soluble starch, 0.5% glucose, 0.5% polypeptone, 0.5% beef extract, 0.25% yeast extract, 0.25% sodium chloride and demineralized water (pH 7.0 before sterilization) and incubated at 28° C. for 48 hours under stirring of 180 r.p.m.

Each 800 ml of the above germinated broth were inoculated in a 30-liter jar containing 20-liter of a medium (2.4% tomato paste, 2.4% dextrin, 1.2% dry yeast, 0.0006% cobalt chloride 6 hydrate and water (pH 7.0 before sterilization)) and incubated at 28° C. for 65 hours with aeration of 20 liter/minute, internal pressure 0.2 kg/cm$^2$G and stirring of 150–350 r.p.m.

(b) Isolation process

The fermentation broth (160 liter) obtained in the above process was mixed with a solution of benzyldimethylcetyl ammonium chloride (1.2%) in methylene chloride (40 liter) to move the active compound into the methylene chloride layer. The layer was extracted with a 3% aqueous solution of sodium iodide (3 liter) and lyophilized to give an active crude powder (60 g). The product (20 g) was subjected to gel filtration with Biogel P-2 (600 ml, Biorad Co. & Ltd.) eluted with water. The fractions showing activity against *Escherichia coli* were collected and lyophilized to give an active product (17.7 g). The product (5.3 g) was applied to gradient chromatography on QAE-SephadexA-25 (Pharmacea Co. & Ltd.) eluted with 0.03–0.3% sodium chloride solution containing 0.05% ammonium chloride to give C fraction (290 ml), B fraction (130 ml) and A fraction (330 ml) successively.

(c) Purification process

Fraction A was adjusted to pH 6, condensed under reduced pressure and desalted on a column of Biogel P-2 (250 ml). The obtained solution was adjusted to pH 6.5 and lyophilized to give a crude powder (230 mg) of PA-41746-A. Fraction B was condensed under reduced pressure, desalted on a column of Biogel P-2 and the active fraction was lyophilized. The product was applied to a column chromatography on Dia ion HP-20AG (130 ml, Mitsubishi Kasei Co., Ltd.) pretreated with 10% sodium chloride eluted with 10% sodium chloride. The active fraction was condensed, desalted on a column of Biogel P-2 and lyophilized to give a powder (20 mg) of PA-41746-B sodium salt. Fraction C was desalted on a column of Biogel P-2, adjusted to pH 6.4, condensed under reduced pressure and lyophilized to give an active substance (172 mg). The product was applied to chromatography on a column of HP-20AG eluted with 10% sodium chloride in the same manner as in fraction B. The fraction containing PA-41746-C was desalted on a column of Biogel P-2. The active fractions were collected, adjusted to pH 6.4, condensed under reduced pressure and lyophilized to give a powder (15 mg) of PA-41746-C sodium salt.

What we claim is:

1. A compound of the formula

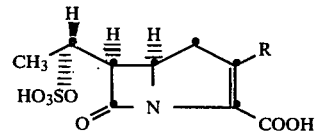

wherein R is carboxymethylsulfinyl (PA-41746-B) or formylsulfinyl (PA-41746-C) and the pharmaceutically acceptable salts thereof.

2. A compound claimed in claim 1 wherein R is carboxymethylsulfinyl (PA-41746-B).

3. A compound claimed in claim 2 wherein R is formylsulfinyl (PA-41746-C).

* * * * *